United States Patent

Carlucci et al.

[11] Patent Number: 5,921,254
[45] Date of Patent: Jul. 13, 1999

[54] POWER FLOSSING DEVICE

[75] Inventors: Vito J. Carlucci; Harold R. Taylor, both of Stratford, Conn.

[73] Assignee: Conair Corporation, Stamford, Conn.

[21] Appl. No.: 09/059,551

[22] Filed: Apr. 13, 1998

[51] Int. Cl.[6] .................................................. A61C 15/04
[52] U.S. Cl. ........................................................ 132/322
[58] Field of Search ................................. 132/322, 325, 132/326, 327

[56] References Cited

U.S. PATENT DOCUMENTS

| | | | |
|---|---|---|---|
| 3,421,524 | 1/1969 | Waters | 132/322 |
| 4,605,025 | 8/1986 | McSpadden . | |
| 5,016,660 | 5/1991 | Boggs . | |
| 5,033,150 | 7/1991 | Gross et al. | 132/322 |
| 5,170,809 | 12/1992 | Imai et al. . | |
| 5,279,314 | 1/1994 | Poulos et al. . | |
| 5,647,385 | 7/1997 | Zebuhr . | |

Primary Examiner—Gene Mancene
Assistant Examiner—Eduardo C. Robert
Attorney, Agent, or Firm—Ohlandt, Greeley, Ruggiero & Perle

[57] ABSTRACT

A power flossing device having only seven parts, namely, a driver element, a driver arm, a flossing head, a retainer, a housing, a seal and a glamour cap. The driver arm is coupled with the driver element and the flossing head. The driver element is responsive to rotary motion provided by a power source to impart to the driver arm both an oscillatory motion along its length dimension and a wobbling motion component transverse to the length dimension. This results in elliptical motion of a length of floss held by the flossing head. The driver element is a unitary structure that has an eccentric hole into which the driver arm is slidably situated to produce the wobbling motion as the driver element revolves and further has a cam follower that coacts with a cam on the driver arm to produce the oscillatory motion. The driver arm and cam is also a unitary structure.

9 Claims, 2 Drawing Sheets

POWER FLOSSING DEVICE

FIELD OF INVENTION

This invention relates to dental flossing tools and, in particular, to power dental flossing tools having a multidimensional flossing motion.

BACKGROUND OF INVENTION

Dental floss is a widely prescribed dental cleaning aid. Proper use of dental floss is essential for thorough cleaning of the teeth. Proper manual flossing includes horizontal motion of the floss until the floss passes through the contact point between two adjacent teeth, followed primarily by vertical movement of the floss to clean the adjacent teeth once the floss is in the interproximal area.

Power flossing devices are known to have horizontal vibration of the floss for entry of the floss into the interproximal area, as well as an up and down motion of some type when the floss has entered the interproximal area. Typical power flossing devices are described in U.S. Pat. Nos. 5,279,314, 5,170,809 and 5,016,660 and the patents referenced in each.

Many of these prior art power flossing devices contain many parts and are difficult to assemble. This results in a large number of parts and considerable labor for assembly, which translates into high prices for consumers. For instance, the motion translation assembly of the power flossing device described in U.S. Pat. No. 5,279,314, includes a cam body 70, yoke 80, and body portion 104, each to fit within particular slots situated in top and bottom sections 62 and 64.

SUMMARY OF THE INVENTION

An object of this invention is to provide a novel power flossing device that has a small number of parts and is capable of assembly with minimal labor.

Another object is to provide a power flossing device that uses only two parts to convert rotary motion into multidimensional motion.

Briefly, a dental flossing device embodying the present invention has a motion translator that includes a driver element and an elongated driver arm. The driver arm is coupled with the driver element and a flossing head. The driver element is responsive to rotary motion provided by a power source to impart to the driver arm both an oscillatory motion along its length dimension and a wobbling motion component transverse to the length dimension. This results in elliptical motion being imparted to a length of floss held by the flossing head.

The driver element is preferably a unitary structure that has an eccentric hole into which the driver arm is slidably situated to produce the wobbling motion as the driver element revolves. The driver element further has a cam driver that coacts with a cam follower on the driver arm to produce the oscillatory motion. The driver arm and cam follower are also preferably a unitary structure.

BRIEF DESCRIPTION OF THE DRAWINGS

In the drawings, like reference characters denote like elements of structure

DESCRIPTION OF PREFERRED EMBODIMENT

Figure 1:
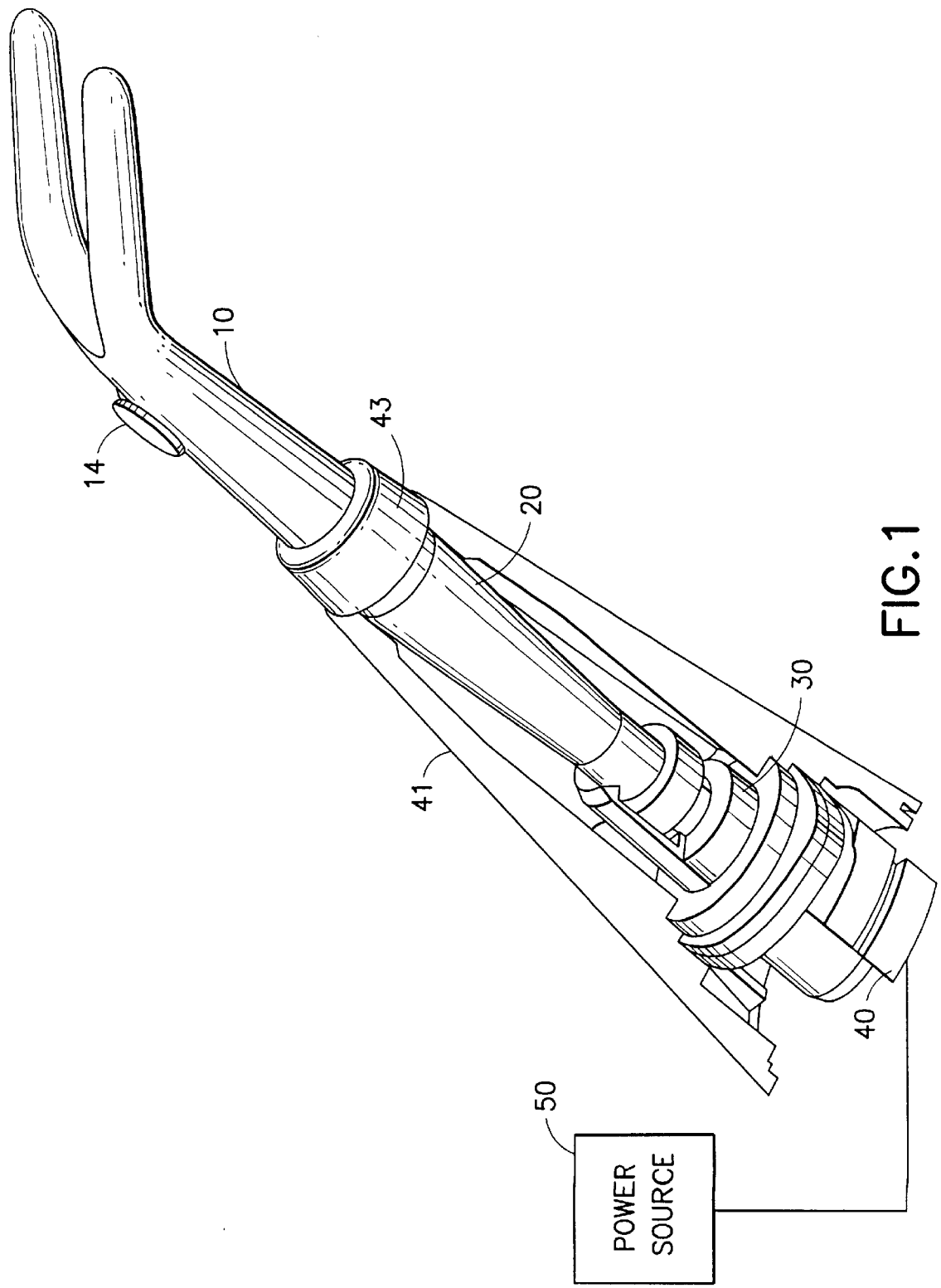
FIG. 1 is a combination perspective and block diagram view of a flossing assembly embodying the invention.
Figure 2:
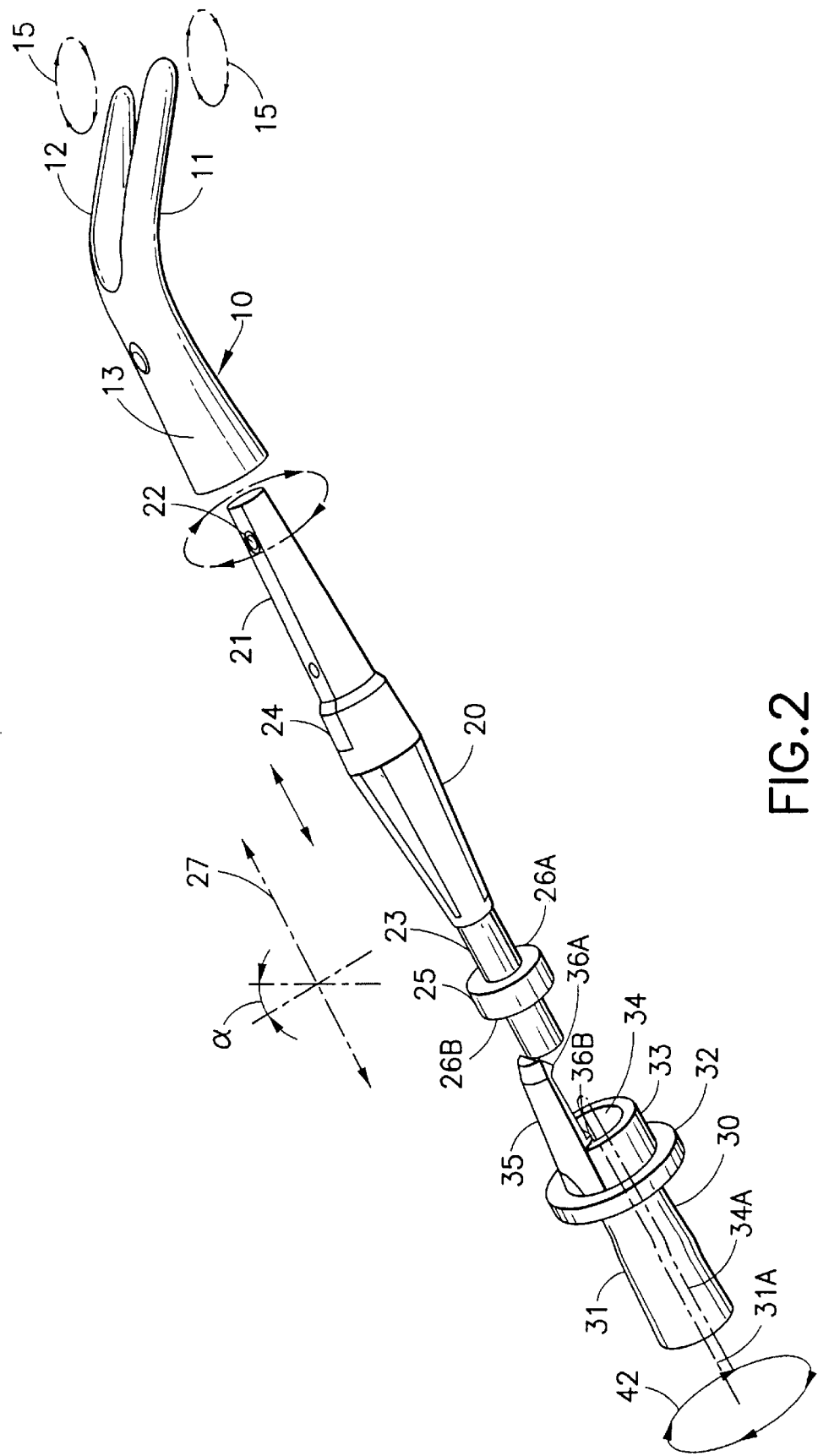
FIG. 2 is perspective and exploded view of the flossing assembly of FIG. 1, without the housing, bearing retainer and seal.

With reference now to FIGS. 1 and 2, power operated dental flossing apparatus embodying the invention has a flossing head 10 coupled via an elongated driver arm 20 to a driver element 30. Flossing head 10, driver arm 20 and driver element 30 form a motion translation assembly. The motion translation assembly is enclosed in a housing 41 (shown in FIG. 1 only) which is partially broken away for illustration purposes. A bearing retainer 40 is provided to retain driver element 30 and driver arm 20 by pressing into housing 41 in a snap lock manner by snap action means (not shown).

A seal 43 is arranged about the joiner of housing 41 and flossing head 10 to prevent evaporation of lubricant from within housing 41 and also to prevent saliva and water from entering housing 41. To complete the assembly, a glamour cap (not shown) is fitted to the open end of housing 41 for purpose of cover and identification, as by color for different users.

Bearing retainer 40 is adapted for connection to a power source 50 which may be a standard dental brushing or flossing power source which, when turned, on produces a rotary motion that causes bearing retainer 40 and driver element 30 to rotate as illustrated by the rotational arrows 42 in FIG. 2. Housing 41 is contoured to mate with a power toothbrush handle that includes power source 50.

Flossing head 10 in the illustrated embodiment is shown as having a sling shot shape with spaced apart flossing arms 11 and 12 joined to a stem 13. Flossing arms 11 and 12 are adapted to receive a length of floss (not shown for clarity purposes). A supply of floss (not shown) is adapted for mounting to an anchor 14. Anchor 14 contains a through hole for purposes of attachment to driver arm 20. Flossing arms 11 and 12 are arranged to hold the length of floss in a direction transverse or orthogonal to the length dimension 27 of the driver arm 20.

Referring to FIG. 2, driver arm 20 has an upper portion 21 which is coupled to flossing head 10 at 22 by a suitable fastener which may be a screw (not shown) threaded through anchor 14 and a lower portion 23 which is coupled to driver element 30 as described below. Upper and lower portions 21 and 23 are joined together by a sliding pivot 24. A cam means, shown as a canted collar 25, having an upper cam surface 26A and a lower cam surface 26B is arranged about lower arm portion 23. Cam surfaces 26A and 26B are in parallel planes at a slight angle α to an orthogonal extrending from the length dimension 27 of driver arm 20 (as illustrated in FIG. 2). Preferably lower arm portion 23, including canted collar 25, is a unitary structure.

Driver element 30 is preferably a unitary structure having a lower shaft 31, flange 32, upper shaft 33 and a cam driver 35. Lower shaft 31 is arranged for connection to power source 50 (FIG. 1). Upper shaft 33 contains an axial hole 34 into which lower arm portion 23 of the driver arm 20 is slidably situated. Cam driver 35 extends upwardly from the flange 32 along the length dimension of driver arm 20. Cam driver 35 has an upper cam surface 36A and a lower cam surface 36B which mate with upper and lower cam surfaces 26A and 26B, respectively, of canted collar 25 of driver arm 20. Cam driver 35 and canted collar 25, together, form a means for producing reciprocating longintudinal action.

Axial hole 34 is off center or eccentric relative to lower shaft 31 of driver element 30 as illustrated by center lines 31A of lower shaft 31 and 34A of axial hole 34. The diameter of hole 34 is larger than the diameter of lower arm portion 23 of driver arm 20 to permit driver arm 20 to slide back and forth in hole 34 to enable both oscillatory motion and wobble motion to driver arm 20.

In operation, bearing retainer 40 and driver element 30 rotate in response to rotary motion produced by power source 50. During each revolution, cam driver 35 coacts with cam surfaces 26A and 26B of canted collar 25 to cause driver arm 20 to oscillate back and forth along its length dimension 27. The limits of the oscillatory motion are determined by the angle $\alpha$ (degree of cant of the collar 25).

Wobble motion is imparted to the driver arm 20 by virtue of the eccentricity of the axial hole 34.

The combination of oscillatory motion and wobble motion results in a flossing motion having an elliptical orbit as illustrated by the arrows 15.

The dental flossing device of this invention is characterized by a small number of parts that are easily assembled with minimal labor. In particular, the parts count is seven, namely, the flossing head 10, the driver arm 20, the driver element 30, the bearing retainer 40, seal 43, glamour cap and housing 41. These parts are readily assembled with minimum labor.

Modifications can be made to the illustrated embodiment without departing from the spirit of the invention. Accordingly, the preferred embodiment is illustrative only and is not intended to limit the scope of the invention.

What is claimed is:

1. A dental flossing device comprising:

a power source for producing rotary motion;

a flossing head; and motion translation means having a driver arm and a driver element, said driver arm exhibiting a length dimension and having one end coupled with the flossing head, the driver element being responsive to the rotary motion to impart to the driver arm and the flossing head both an oscillatory motion along said length dimension and a wobbling motion which causes said one end of said driver arm to translate about a closed, nonlinear path that lies in a plane transverse to said length dimension.

2. A dental flossing device in accordance with claim 1 and further comprising a cam driver and a cam follower situated on the driver element and the driver arm, respectively, and arranged to provide said oscillatory motion.

3. A dental flossing device in accordance with claim 2 wherein the driver element contains an off center hole into which the driver arm is slidably situated and the driver element when rotated imparts said wobbling motion to the driver arm.

4. A dental flossing device in accordance with claim 3 wherein the driver element is a unitary structure.

5. A dental flossing device in accordance with claim 4 wherein the flossing head has two spaced apart arms adapted to hold a length of floss orthogonal to the length dimension of the driver arm.

6. A motion translation assembly for a power dental treatment device wherein the assembly responds to rotary motion produced by a power source to impart a reciprocating motion to a dental treatment heads said assembly comprising:

a driver element adapted to rotate in response to the power source; and a driver arm that exhibits a length dimension and has one end coupled with the dental treatment head, the driver element being responsive to the rotary motion to impart to the driver arm and the dental treatment head both an oscillatory motion along said length dimension and a wobbling motion component which causes said one end of said driver arm to translate about a closed, nonlinear path that lies in a plane transverse to said length dimension.

7. A motion translation assembly in accordance with claim 6 wherein said driver element is a unitary structure having a shaft with an off center axial hole; and said driver arm is slidably situated in said off center hole in such a manner as to wobble when the driver element rotates.

8. A motion translation assembly in accordance with claim 7 and further comprising a cam driver and a cam follower situated on the driver element and the driver arm, respectively, and arranged to provide said oscillatory motion.

9. A motion translation assembly in accordance with claim 8 wherein the dental treatment head is a flossing head which has two spaced apart arms adapted to hold a length of floss orthogonal to the axial direction of the driver arm.

* * * * *